United States Patent [19]

Hanifl

[11] Patent Number: 5,151,094
[45] Date of Patent: Sep. 29, 1992

[54] SUCTION SWAB

[75] Inventor: Paul H. Hanifl, Barrington, Ill.

[73] Assignee: Sage Products, Inc., Crystal Lake, Ill.

[21] Appl. No.: 496,423

[22] Filed: Mar. 20, 1990

[51] Int. Cl.$^5$ ............................................. A61C 17/04
[52] U.S. Cl. ................................... 604/902; 604/118; 604/129; 433/91
[58] Field of Search .................. 433/91, 93; 604/1, 2, 604/118, 129, 48, 54, 73, 902

[56] References Cited

U.S. PATENT DOCUMENTS

| | | | |
|---|---|---|---|
| D. 282,698 | 2/1986 | Newton | D4/104 |
| 2,180,249 | 11/1939 | Lempert | 32/33 |
| 2,490,168 | 12/1949 | Strauss | 128/269 |
| 2,637,106 | 4/1953 | Otis | 32/33 |
| 3,324,855 | 6/1967 | Heimlich | 128/269 |
| 3,495,917 | 2/1970 | Truhan | 401/132 |
| 3,519,364 | 7/1970 | Truhan | 401/177 |
| 3,520,300 | 7/1970 | Flower | 128/276 |
| 3,758,950 | 9/1973 | Krouzian | 433/91 |
| 4,233,025 | 11/1980 | Larson | 433/136 |
| 4,356,823 | 11/1982 | Jackson | 604/902 |
| 4,522,592 | 6/1985 | Johnson | 604/902 |
| 4,787,599 | 11/1988 | Nyboer | 604/902 |

Primary Examiner—Stephen C. Pellegrino
Assistant Examiner—Michael Rafa
Attorney, Agent, or Firm—Lee, Mann, Smith, McWilliams, Sweeney & Ohlson

[57] ABSTRACT

A disposable suction swab formed from an elongated stem shaped at one end for connecting to a suction source and having at the opposite end an enlarged, resilient tip. A transverse aperture is formed in the tip is registration with a hole in the stem, the aperture being larger in cross section than the hole. Means is provided for controlling suction within the stem to thereby control the amount of suction in the aperture in the tip.

24 Claims, 1 Drawing Sheet

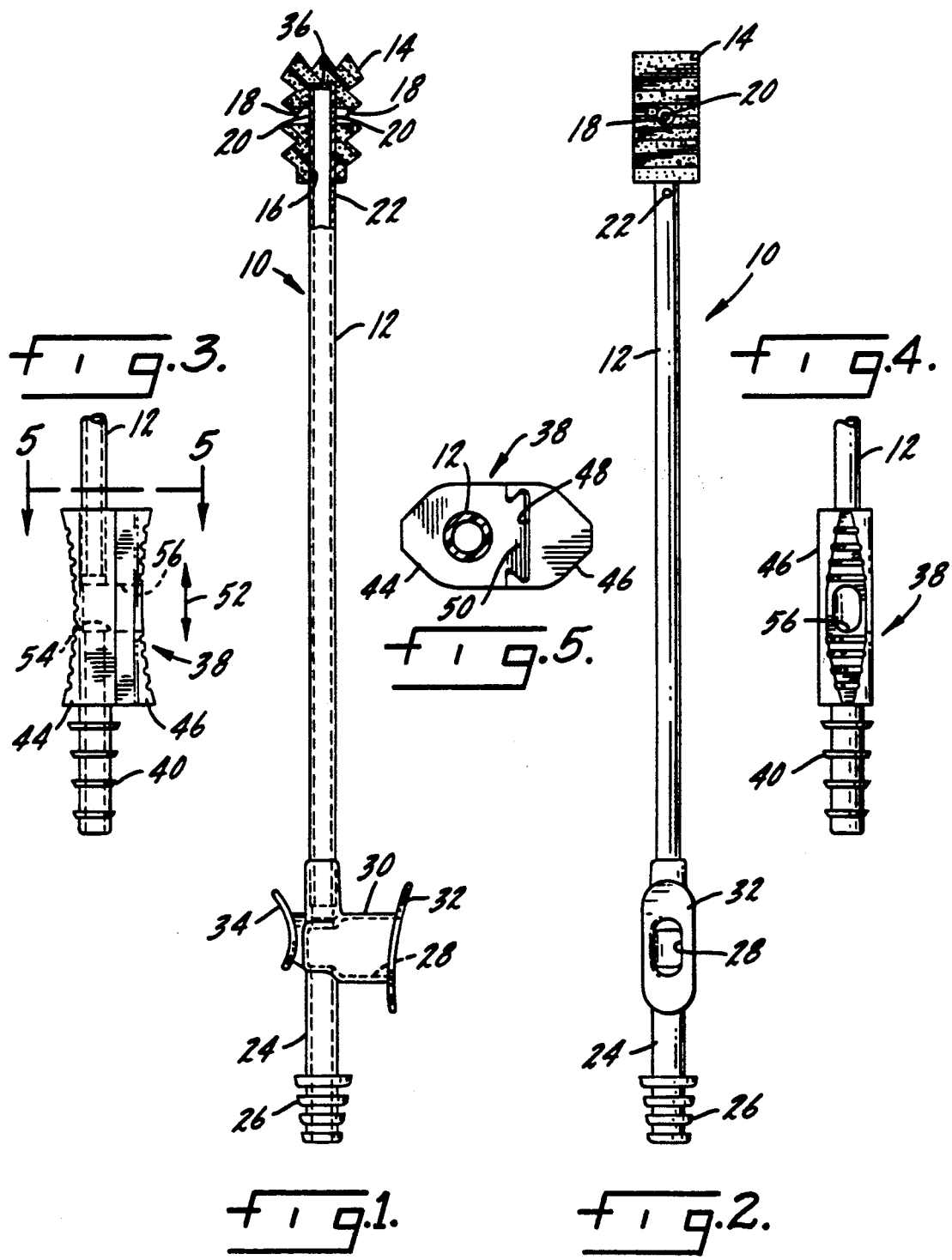

SUCTION SWAB

BACKGROUND OF THE INVENTION

This invention relates to oral swabs, and in particular to a swab configured so that suction can be applied to the swab to eliminate mucus or other liquid matter encountered.

Oral swabs are used for mouth care, normally during oncology treatments, treating patients in intensive care and treating patients on respirators. A swab, used by the assignee of the present application for several years, is depicted in U.S. Design Pat. No. D 282,698, issued Feb. 25, 1986. When the swab has been used, it is discarded.

Previous swabs, such as that described immediately above, have limited use since once the swab is saturated or coated with oral fluids, such as saliva and mucus, the swab is no longer of any utility, and must be discarded. Thus, several swabs might be required for a very simple process or operation.

Oral suction devices are known, as depicted in U.S. Pat. Nos. 2,180,249; 2,637,106; 3,520,300; and 4,233,025. Similar devices, but used for application purposes (and therefore having flow in the opposite direction) are depicted in U.S. Pat. Nos. 2,490,168; 3,324,855; 4,495,917; and 3,519,364. Such devices are generally quite complicated, are normally not disposable (unless having a disposable portion), and are therefore not sanitary without sterilization.

SUMMARY OF THE INVENTION

The present invention is directed to a disposable suction swab. The swab has an elongated, hollow stem, with means at one end of the stem for connecting the stem to a source of suction. Means is also provided for controlling suction within the stem. An enlarged, resilient tip is mounted on the other end of the stem, the tip having a longitudinal channel accommodating the stem and at least one transverse aperture connected to the central channel. A hole is located in the stem in registration with the aperture, the aperture being larger in cross-section than the hole. The tip is appropriately secured to the stem.

In accordance with the preferred form of the invention, the aperture and the hole are circular, with the aperture having a diameter about twice the diameter of the hole. Preferably, there are two of the apertures in axial alignment with one another with an appropriate hole in the stem in registration with each aperture.

The end of the stem on which the tip is mounted is closed. In accordance with one form of the invention, a plug is installed in that end. In another form of the invention, the end is closed by means of a collection of adhesive which is used to secure the tip to the stem.

BRIEF DESCRIPTION OF THE DRAWING FIGURES

The invention is described in greater detail in the following description of an example embodying the best mode of the invention, taken in conjunction with the drawing figures, in which:

FIG. 1 is a side elevational illustration of the invention, partly in cross section to show detail;

FIG. 2 is a top plan view of the swab according to the invention;

FIG. 3 is a side elevational illustration of a second form of the suction port according to the invention;

FIG. 4 is a top plan view thereof; and

FIG. 5 is a cross sectional view taken along lines 5—5 of FIG. 3.

DESCRIPTION OF EXAMPLES EMBODYING THE BEST MODE OF THE INVENTION

A disposable suction swab according to the invention is shown generally at 10 in the drawing figures. The swab 10 is composed of an elongated, hollow stem 12 on which an enlarged, resilient tip 14 is mounted. The stem 12 may be of plastic, and the tip 14 is preferably made of a pliant foam or other similar, soft structure which is at least somewhat absorbent and which will not injure soft tissue in the mouth. The tip 14 may be ribbed as shown or formed otherwise to promote scrubbing and to aid in the removal of saliva, mucus and other liquid and semi-liquid material.

The tip 14 has a longitudinal central channel 16 which accommodates the stem 12, and includes a transverse aperture 18 connected to the central channel 16. It is preferred that the aperture 18 be through the depth of the tip 14, thus forming a pair of apertures in axial alignment with one another. A hole 20 is formed in the stem 12 in registration with each aperture 18. Again, since the apertures 18 are preferably axially aligned, the holes 20 are likewise aligned.

The apertures 18 and holes 20 are circular in cross section. As shown in the drawing figures, the apertures 18 are larger in cross section than the holes 20, so that ropy mucus and other similar, difficult liquids can readily enter the aperture 18 and be sucked through the hole 20 into the stem 12. It is preferred that the aperture 18 has a diameter about twice that of the hole 20 for proper functioning of the swab 10, the aperture 18 being about 2 mm or smaller in dimension.

A second hole 22 or series of holes, can be located in the stem 12 immediately at the base of the tip 14. The hole 22 is close enough to the tip 14 to be protected by the bulk of the tip. If the hole 22, is spaced too far from the tip 14, the utility of the swab 10 is greatly diminished because the swab must be inserted too far in a patient's mouth for proper suction.

The end of the swab 10 opposite from the tip 14 is installed within a suction port 24. The suction port 24 includes a connector 26 having circumferential ribs shaped to engage a flexible plastic tube or the like (not illustrated) which is connected to a source of suction. The suction port 24 also includes an opening 28 in communication with the hollow interior of the suction port 24 and stem 12, the opening 28 being surrounded by a guard 30 which is topped by a platform 32 shaped to be engaged by the finger or thumb of a user of swab 10. A second platform 34 is formed on the opposite side of the suction port 24 for ease of gripping by the user. By judicious adjustment of a thumb or finger on the platform 32, the degree of suction at the holes 20 can be controlled by controlling the size of the opening 28.

The suction port 24 is preferably adhesively or otherwise permanently secured to the stem 12. Similarly, the tip 14 is preferably adhesively or otherwise attached to the stem 12. Because the stem 12 is hollow, the end of the stem 12 is plugged, as shown at 36, either with a separate plug, or with a collection of adhesive which is also used for securing the tip 14 to the stem 12.

The swab 10 is preferably formed by attaching the suction port 24 (which aay be injection-molded from plastic) to the stem 12. The tip 14, with the aperture 18 already formed therein, is injected with an appropriate adhesive, such as a hot melt adhesive, and is then installed on the end of the stem 12. Thereafter, the holes 20 are then drilled or punched through the stem 12 to complete the swab 10. If the hole 22 is employed, it may be formed at the same time as the hole 20, or may be previously formed in the stem 12, since there is little likelihood that adhesive used for securing the tip 14 to the stem 12 would invade and therefore clog the hole 22.

A second form of suction port 38, in place of the suction port 24, is shown in FIGS. 3-5. The suction port 38 includes a connector 40 having circumferential ribs shaped to engage a flexible plastic tube or the like (not illustrated) which is connected to a source of suction, in precisely the same manner as the suction port 24. The suction port 38 is composed of a stationary portion 44 and a slide 46 mounted thereon. As shown in FIG. 5, the slide 46 includes a channel 48 along its length which engages an upstanding trapezoidal guide 50 forming a part of the stationary portion 44. Thus, the slide 46 may be moved along the stationary portion 44 in either direction as shown by the arrow 52 in FIG. 3.

The stationary portion 44 includes an opening 54 and the slide 46 includes an opening 56. As shown in FIG. 3, the openings 54 and 56 may be aligned with one another or, as the slide 46 is moved in either direction, the opening 56 is moved out of direct alignment with the opening 54 until the openings are no longer aligned, at which time entry of air into the opening 54 is prevented by the solid structure of the slide 46. With the openings 54 and 56 thus not aligned, full suction is available at the holes 20, while partial or full alignment of the openings 54 and 56 diminishes suction at the hole 20 commensurately.

As with the suction port 24, with the slide 46 aligned with the stationary portion 44 as shown in FIG. 3, suction may also be controlled by placing a thumb or finger over the opening 56 to control the size of the opening. Thus, suction is controlled by either moving the slide 46, controlling the size of the opening 56 with a thumb or finger, or a combination of the two.

In the same fashion as the suction port 24, the suction port 38 is adhesively or otherwise permanenty secured to the stem 12. The suction port 38 may be of injection-molded plastic, with the parts 44 and 46 separately formed and assembled.

The invention provides a simple yet effective suction swab which, due to the greater size of the aperture 18 in relation to the hole 20, largely avoids clogging and therefore premature failure of the swab. Various changes can be made to the swab without departing from its utility. In addition to the auxiliary hole or holes 22, more than one axial aperture 18 and corresponding hole 20 can be formed in the tip 14, and may be crosswise in relation to the illustrated holes 20 and apertures 18. In addition, although the suction ports 24 and 38 are preferably injection-molded parts, the openings 28 and 54/56 and respective connectors 26 and 40 can be formed in separate parts, and indeed, the opening 28 or 54 may be a simple transverse opening in the stem 12 and still achieve a reasonable degree of suction control. Various changes can be made to the invention without departing from the spirit thereof or scope of the following claims.

What is claimed is:

1. A disposable suction swab, comprising
   a. an elongated, hollow stem having opposite ends,
   b. means at one end of said stem for connecting said stem to a source of suction,
   c. means for controlling suction within said stem,
   d. an enlarged, solid and resilient tip mounted on the other end of said stem, said tip having a longitudinal central bore accommodating said stem and at least one transverse aperture connected to said central bore,
   e. a hole in said stem contiguous to and in axial alignment with said aperture, said aperture being larger in cross-section than said hole, and
   f. means securing said tip to said stem.

2. A suction swab according to claim 1 in which said aperture and said hole are circular, said aperture having a diameter about twice the diameter of said hole.

3. A suction swab according to claim 1 including two of said apertures in axial alignment with one another.

4. A suction swab according to claim 3 including a said hole in said stem in alignment with each said aperture.

5. A suction swab according to claim 1 including two of said apertures and a said hole in said stem in alignment with each said aperture.

6. A suction swab according to claim 1 in which said means securing comprises an adhesive.

7. A suction swab according to claim 1 including means closing said stem at said other end.

8. A suction swab according to claim 7 in which said means closing comprises a plug.

9. A suction swab according to claim 7 in which said means closing comprises a collection of adhesive.

10. A suction swab according to claim 1 in which said connecting means and said means for controlling suction are unitary.

11. A suction swab according to claim 1 in which said means for controlling suction comprises an opening to said stem and a guard surrounding said opening.

12. A suction swab according to claim 11 including a platform on said guard shaped to be engaged by a finger or thumb for selectively regulating the size of said opening.

13. A suction swab according to claim 1 in which said means for controlling suction comprises an opening to said stem and a valve to regulate the size of said opening.

14. A suction swab according to claim 13 in which said valve includes a slide moveable across said opening to regulate the size of said opening.

15. A disposable suction swab, comprising
    a. an elongated, hollow stem having opposite ends,
    b. means at one end of said stem for connecting said stem to a source of suction,
    c. means for controlling suction within said stem,
    d. an enlarged, solid and resilient tip mounted on the other end of said stem, said tip having a longitudinal central bore accommodating said stem and a transverse aperture passing through said tip and connected to said central bore,
    e. a hole through said stem contiguous to and in axial alignment with said aperture, said aperture being larger in cross-section than said hole, and
    f. means securing said tip to said stem.

16. A suction swab according to claim 15 in which said aperture and said hole are circular, said aperture having a diameter about twice the diameter of said hole.

17. A suction swab according to claim 15 in which said means securing comprises an adhesive.

18. A suction swab according to claim 15 including means closing said stem at said other end.

19. A suction swab according to claim 18 in which said means closing comprises a plug.

20. A suction swab according to claim 18 in which said means closing comprises a collection of adhesive.

21. A suction swab according to claim 15 in which said means for controlling suction comprises an opening to said stem and a guard surrounding said opening.

22. A suction swab according to claim 21 including a platform on said guard shaped to be engaged by a finger or thumb for selectively regulating the size of said opening.

23. A suction swab according to claim 15 in which said means for controlling suction comprises an opening to said stem and a valve to regulate the size of said opening.

24. A suction swab according to claim 23 in which said valve includes a slide moveable across said opening to regulate the size of said opening.

* * * * *